US005619987A

United States Patent [19]

Matsuoka

[11] Patent Number: 5,619,987

[45] Date of Patent: Apr. 15, 1997

[54] SEMI-CLOSED REBREATHING APPARATUS WITH WATER REMOVING PUMP

[75] Inventor: Shunsuke Matsuoka, Chiba, Japan

[73] Assignee: Grand Bleu International, Inc., New York, N.Y.

[21] Appl. No.: 276,875

[22] Filed: Jul. 18, 1994

Related U.S. Application Data

[63] Continuation of Ser. No. 33,649, Mar. 17, 1993, abandoned, which is a continuation-in-part of Ser. No. 862,207, Apr. 2, 1992, abandoned.

[30] Foreign Application Priority Data

Sep. 24, 1991 [JP] Japan .................................... 3-270442

[51] Int. Cl.[6] .......................... A61M 16/00; A62B 7/04; A62B 9/02; F16K 31/26

[52] U.S. Cl. ................................ 128/204.29; 128/204.26; 128/205.24; 128/205.22; 128/205.12; 128/205.13; 128/205.16

[58] Field of Search ......................... 128/204.28, 204.29, 128/205.13, 205.17, 200.29, 205.22, 205.28, 207.14, 204.26, 204.18, 205.14, 205.16, 205.24, 205.12; 417/486, 472, 473; 114/183 R, 184

[56] References Cited

U.S. PATENT DOCUMENTS

| | | | |
|---|---|---|---|
| 2,818,067 | 12/1957 | Rebikoff et al. . | |
| 2,931,357 | 4/1960 | Arborelius et al. | 128/204.28 |
| 3,021,839 | 2/1962 | Marsh | 128/204.28 |
| 3,316,905 | 5/1967 | Seeler et al. . | |

(List continued on next page.)

FOREIGN PATENT DOCUMENTS

| | | | |
|---|---|---|---|
| 1237217 | 6/1960 | France . | |
| 2418148 | 9/1979 | France . | |
| 2546126 | 5/1983 | France . | |
| 541837 | 7/1926 | Germany | 128/204.28 |
| 548272 | 4/1932 | Germany | 128/204.28 |
| 598691 | 5/1934 | Germany | 128/204.28 |
| 894051 | 10/1953 | Germany | 128/204.28 |
| 902714 | 1/1954 | Germany | 128/204.28 |
| 1060101 | 6/1959 | Germany . | |
| 724400 | 11/1966 | Italy . | |
| 3270442 | 4/1992 | Japan . | |
| 2197793 | 7/1988 | United Kingdom . | |
| 2201602 | 9/1988 | United Kingdom . | |
| 8603171 | 6/1986 | WIPO | 128/204.18 |

OTHER PUBLICATIONS

Excerpted from: LaViolette, P.A. "New Hope for a Safe, Light, Fire Service Breathing Apparatus," *The Fire Independent* vol. 3, No. 1, Mar. 1977.

*Primary Examiner*—Kimberly L. Asher
*Attorney, Agent, or Firm*—Darby & Darby

[57] ABSTRACT

A respiration system including a carbon dioxide absorber, wherein any water located in the exhaled gases, or present in the system due to leakage, is removed from the system before the exhaled gases reach the carbon dioxide absorber. The respiration system includes a supply of pressurized breathable gas connected to a first expansion chamber. A mouthpiece is provided for passing breathable gas to, and receiving exhaled gas from the user. The mouthpiece has an inlet and an outlet wherein the outlet is connected to the first expansion chamber. Means is provided for mixing the exhaled gas within the first expansion chamber with breathable gas from the breathable-gas supply. Water is removed from the exhaled gas in the first expansion chamber. An inhalation tube connects the first expansion chamber and the inlet of the mouthpiece. The inhalation tube provides communication of the gas mixture of the first expansion chamber and the mouthpiece. Means is provided for absorbing at least a portion of the carbon dioxide from the exhaled gases. The absorbing means is located along the inhalation tube between the first expansion chamber and the mouthpiece. A portion of the breathable gas from the breathable-gas supply is introduced to the inhalation tube between the absorbing means and the mouthpiece to compensate for any gas-flow resistance created by the absorbing means during high demand inhalation by the user.

4 Claims, 5 Drawing Sheets

U.S. PATENT DOCUMENTS 3,402,711 9/1968 Emerson ........................ 128/204.28
3,556,098 1/1971 Kanwisher et al. .
3,710,553 1/1973 Parker et al. .
4,168,706 9/1979 Lovell ........................ 128/204.28
4,453,543 6/1984 Kohnke ........................ 128/203.28
4,567,889 2/1986 Lehmann ........................ 128/204.28
4,781,184 11/1988 Fife ........................ 128/205.12
4,813,476 3/1989 Mahefkey ........................ 165/32
5,035,238 7/1991 Christianson ........................ 128/204.26
5,048,517 9/1991 Pasternack ........................ 128/205.28
5,052,384 10/1991 Kaneko ........................ 128/205.14
5,115,804 5/1992 Brookman ........................ 128/201.22
5,143,060 9/1992 Smith ........................ 128/205.28

SEMI-CLOSED REBREATHING APPARATUS WITH WATER REMOVING PUMP

This is a continuation of application Ser. No. 08/033,649, filed Mar. 17, 1993, now abandoned, which was a continuation-in-part of application Ser. No. 07/862,207, filed Apr. 2, 1992, now abandoned.

FIELD OF THE INVENTION

This invention relates to rebreathing equipment, and, more particularly, to semi-closed scuba equipment wherein exhaled carbon dioxide is separated and absorbed within the equipment, thereby leaving a portion of the exhaled gases suitable for rebreathing.

BACKGROUND OF THE INVENTION

A conventional semi-closed rebreathing scuba system is illustrated in FIG. 1 labeled "PRIOR ART". This prior art system 10 includes a supply circuit 12 and a breathing circuit 14. The supply circuit 12 which supplies fresh breathable gas (not yet inhaled) to the breathing circuit 14 includes a pressurized tank 16, a regulator 18 and a flow control device 20. The breathing circuit 14 includes an expandable respiration bellows 22 connected to an inhalation conduit 24 which, in turn, is connected to a mouthpiece assembly 26. An outlet portion of the mouthpiece assembly 26 is connected to an exhalation conduit 28 which reconnects to the respiration bellows 22 through a carbon dioxide absorber 30. The respiration bellows 22 also includes an outlet valve 32 allowing a controlled amount of gas to exit the system (hence the term, semi-closed).

In operation of this prior art rebreathing system, the pressurized air from the supply circuit 12 is introduced into the breathing circuit 14 at the respiration bellows 22. The fresh supply-gas is mixed in the respiration bellows 22 with the exhaled gas that has passed from the diver (not shown) through the outlet side of the mouthpiece assembly 26, the exhalation conduit 28, the carbon dioxide absorber 30 and into the respiration bellows 22. As the diver inhales, the mixed gas from the bellows 22 is forced through the inhalation conduit 24 and the inlet portion of the mouthpiece assembly 26. The mouthpiece assembly 26 includes one-way check valves to prevent the direct rebreathing of any exhaled gas and to otherwise ensure the proper transfer of gases between the diver and the rebreathing equipment. As this breathing cycle is repeated around the breathing circuit 14 of the breathing system 10, waste gases, including carbon dioxide, expired by the diver, are removed from the breathing circuit 14 by the carbon dioxide absorber 30. Waste gas that is removed from the breathing circuit 14 is replaced with a supply of fresh gas from the supply circuit 12. The regulator 18, the flow control device 20, the expandable respiration bellows 22 and the outlet valve 32 work together to ensure that the pressure of the gas within the breathing circuit 14 remains at a constant and safe level regardless of the surrounding environment.

One problem with the above-described prior art semi-closed scuba breathing system relates to the handling of moisture introduced into the breathing circuit 14. Water may enter the breathing circuit 14 in the form of water vapor carried by the exhaled gases of the diver or through a leak in the system from the outside environment. In either case, water has a detrimental effect on the carbon dioxide absorber, effectively reducing the ability of the absorber to remove waste gas from the breathing circuit 14. Any water entering the exhalation conduit 28 of the prior art system of FIG. 1 will pass directly into the carbon dioxide absorber 30, and prematurely render the absorber 30 ineffective. Additionally, water entering the breathing circuit 14 will eventually accumulate in the respiration bellows 22. Depending on the orientation of the diver, the accumulated water in the respiration bellows 22 may easily enter the inhalation conduit 24 of the breathing circuit 14 and endanger the safety of the diver.

It is an object of the invention to provide a semi-closed rebreathing apparatus which overcomes the above-mentioned problems.

It is another object of the invention to provide a semi-closed rebreathing apparatus which automatically removes any water accumulated within the system.

It is yet another object to increase the time span during which a carbon dioxide absorber within a rebreathing system will remain effect.

It is still another object to provide an improved semi-closed rebreathing system for firefighting and other environments.

SUMMARY OF THE INVENTION

A respiration system for use by a scuba diver, firefighter or the like, includes a carbon dioxide absorber. At least a portion of any water contained in the exhaled gases is removed from the system before the exhaled gases reach the carbon dioxide absorber.

The respiration system includes a supply of pressurized breathable gas connected to a first expansion chamber. A mouthpiece is provided for passing breathable gas to, and receiving exhaled gas from the user. The mouthpiece has an inlet and an outlet wherein the outlet is connected to the first expansion chamber. Means is provided for mixing the exhaled gas within the first expansion chamber with breathable gas from the breathable-gas supply. Water is removed from the exhaled gas in the first expansion chamber. An inhalation tube connects the first expansion chamber and the inlet of the mouthpiece. The inhalation tube provides communication of the gas mixture of the first expansion chamber and the mouthpiece. Means is provided for absorbing at least a portion of the carbon dioxide from the exhaled gases. The absorbing means is located along the inhalation tube between the first expansion chamber and the mouthpiece. A portion of the breathable gas from the breathable-gas supply is introduced to the inhalation tube between the absorbing means and the mouthpiece to compensate for any gas-flow resistance created by the absorbing means during high demand inhalation by the user.

DESCRIPTION OF THE PREFERRED EMBODIMENTS

Figure 2:
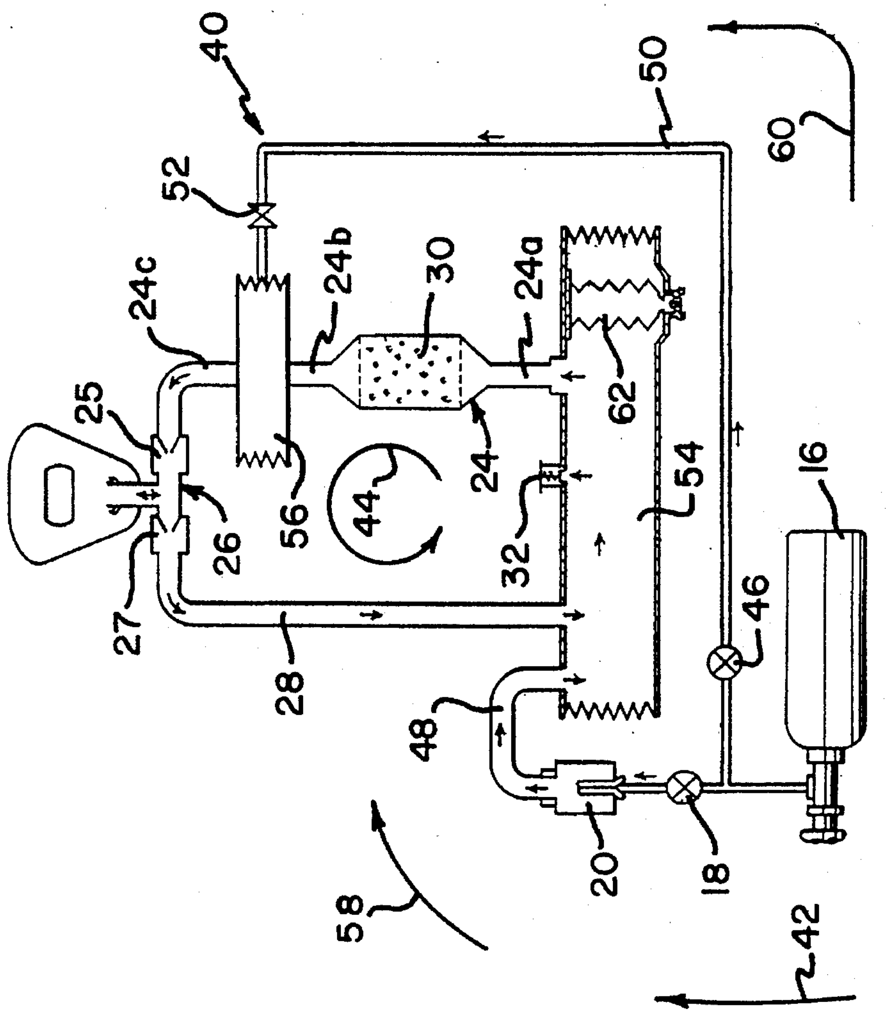
FIG. 2 is schematic of a semi-closed rebreathing system in accordance with a first embodiment of the invention.

Referring to FIG. 2, a schematic of a semi-closed scuba breathing apparatus 40 in accordance with the invention is shown including a supply circuit 42 and a breathing circuit 44. The supply circuit 42 of the present breathing apparatus 40 includes a pressurized tank 16 of a breathable gas such as air or pure oxygen, two regulators 18 and 46, a flow control device 20, a second stage inlet conduit 48, a first stage inlet conduit 50 and an inlet control valve 52.

The breathing circuit 44 of the present breathing apparatus 40 includes a main respiration bellows 54, an inhalation conduit 24, a carbon dioxide absorber 30, an auxiliary bellows 56, a mouthpiece assembly 26 having an inlet port 25 and an outlet port 27, and an exhalation conduit 28. Both the auxiliary respiration bellows 56 and the main respiration bellows 54 are designed to expand and contract between fully expanded and contracted conditions.

The inhalation conduit 24 is made up three segments discussed in greater detail below. A first segment 24*a* is connected between the main bellows 54 and the carbon dioxide absorber 30. A second segment 24*b* is connected between the absorber 30 and the auxiliary bellows 56, and finally a third segment 24*c* is connected between the auxiliary bellows 56 and the inlet port 25 of the mouthpiece assembly 26.

The supply circuit 42 supplies a breathable gas to the breathing circuit 44 at two different points, along two supply paths, respectively, a low pressure path 58 and a high pressure path 60. Along the low pressure path 58 breathable gas from the tank 16 passes through appropriate high-pressure conduit, through a regulator 18, through a flow control device 20, and finally to the main respiration bellows 54 via the second stage inlet conduit 48 which is connected to the outlet of the flow control device 20.

Along the high pressure supply path 60, breathable gas passes from the tank 16 through a regulator 46 and then through a first stage inlet conduit 50 supplying high pressure gas to the auxiliary bellows 56, the flow of which being controlled by the inlet control valve 52.

The main respiration bellows 54 includes an outlet valve 32 for permitting a controlled amount of gas exit from the breathing circuit 44 and enter the outside environment. The main respiration bellows 54 also includes a water removal system 62 for removing any accumulated water from the breathing circuit 44 before the water reaches the carbon dioxide absorber 30 or becomes inhaled by the diver. The water removal system 62 is described in greater detail below.

As the diver breathes normally, his exhaled gases leave the mouthpiece assembly through the outlet port 27 and enter directly into the main respiration bellows 54 by way of the exhalation conduit 28. The exhaled gases are mixed in the main respiration bellows 54 with fresh breathable gas entering the breathing circuit 44 from the low pressure supply path 58 of the supply circuit 42. Any water vapor or liquid carried by the exhaled gas into the main respiration bellows 54 will accumulate and will eventually be removed by the water removal system 62, as described below.

The exhaled gas and fresh gas mixture continue the breathing circuit 44 by being forced through the inhalation conduit 24, through the carbon dioxide absorber 30 and into the auxiliary respiration bellows 56. Any waste gases from the exhaled/fresh gas mixture, especially carbon dioxide are effectively removed from the breathing circuit by the carbon dioxide absorber 30, as is known. The gas leaving the carbon dioxide absorber 30 is clean and breathable.

In completing the breathing circuit 44, the now fully breathable gas enters the auxiliary respiration bellows 56 and, depending on the inhalation demand (described in detail below) may or may not be supplemented by additional fresh breathable gas from the high pressure path 60 before entering the inlet port 25 of the mouthpiece assembly 26 to be inhaled and used by the diver again. The fresh gas entering from the high pressure path 60 is regulated by the inlet control valve 52. The inlet control valve 52 is "open" only when the auxiliary respiration bellows 56 is in its contracted state, i.e., when inhalation demand is high.

Figure 3:
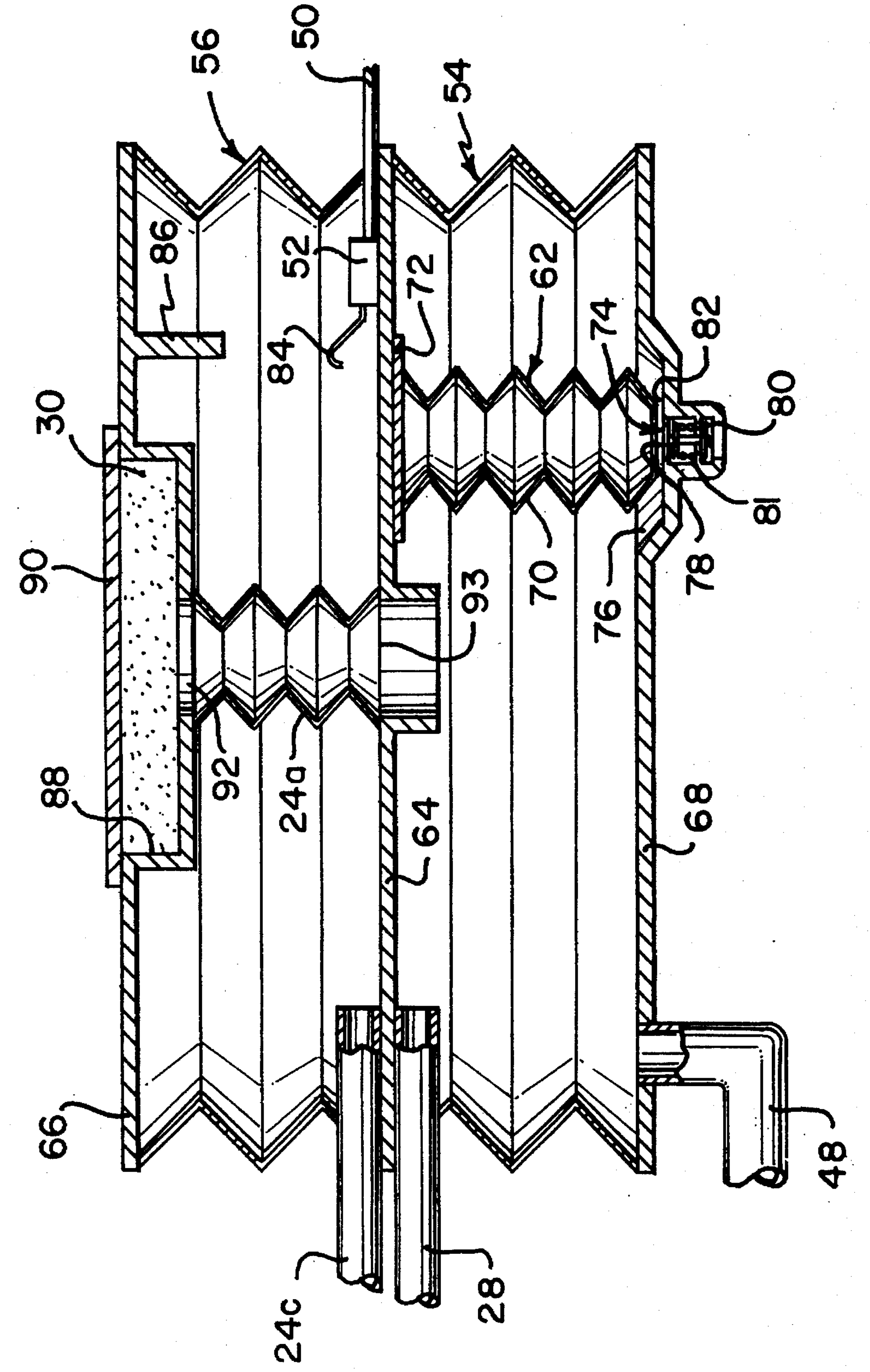
FIG. 3 is a sectional view of a respiration bellows assembly in accordance with another embodiment of the invention.

Referring to FIG. 3, a preferred embodiment of the rebreathing apparatus 40 is shown including the main respiration bellows 54 combined with the auxiliary bellows 56 in a practical, compact unit. A center support plate 64 functions as an end support for both the main and the auxiliary respiration bellows 54, 56, respectively. The auxiliary respiration bellows 56 further includes an upper end plate 66. The main respiration bellows 54 further includes a lower end plate 68. Appropriate flexible bellows material is affixed to the upper end plate 66 and an upper side of the center support plate 64 to form the auxiliary respiration bellows 56. Similarly, the main respiration bellows is formed with the bellows material attached to a lower side of the center support plate 64 and the lower end support 68.

The water removal system 62, introduced above, includes a pumping bellows 70 having a sealed upper end 72 and an open lower end 74. The pumping bellows 70 is positioned within the main respiration bellows 54 and operates as the main respiration bellows 54 expands and contracts. The upper end 72 of the pumping bellows 70 is affixed to the lower side of the center support plate 64. The lower end plate 68 includes an integrally formed collection recess 76 which is the lowest point within main respiration bellows 54. Any water located within the breathing circuit 44 will eventually (prior to the water reaching either the diver or the carbon dioxide absorber 30) collect in the collection recess 76 as long as the orientation of the diver for any short period of time permits gravity to pull the water into the collection recess 76. An opening 78 is located in the lower end plate 68 of the main bellows 54, positioned within the collection recess 76, preferably at the center of the recess 76. Mounted within the opening 78 is located a spring-loaded, one-way valve 80. The one-way valve 80 only permits fluid flow (either gas or liquid) to pass out of the breathing circuit 44 when the pressure acting on the inner side of the valve 80 is greater than both the force of the return spring 81 and the acting pressure of the outside environment.

The pumping bellows 70 is positioned within the main respiration bellows 54 so that its open lower end 74 resides within the collection recess 76 centered about the opening 78 and the one-way valve 80. The pumping bellows 70 operates between a fully expanded state and a fully compressed state. The length of the pumping bellows 70 when it is in its fully expanded state, as shown in FIG. 3, is preferably slightly less than the distance between the center support plate 64 and the lower end plate 68 of a fully expanded main respiration bellows 54, as measured from within the collection recess 76 (and effectively equals the length of the main bellows 54, fully expanded). The difference in the expanded lengths between the main bellows 54 and the pumping bellows 70 defines an inlet gap 82 through which unwanted water collected within the collection recess 76 may pass, thereby entering the pumping bellows 70.

Alternatively, the pumping bellows 70 may extend fully from the center support plate 64 to the lower end plate 68. In this case, the lower end of the pumping bellows 70 would be provided with slits or other means for permitting entry of water from the main respiration bellows 54 into the pumping bellows 70.

In operation of the water removal system 62, as the main bellows 54 expands and contracts, the pumping bellows 70, being tightly positioned between the lower end plate 68 and the center support plate 64, is forced to also expand and contract. During expansion, the pressure within the pumping bellows 70 will invariably be less than the pressure within the main bellows 54 (effectively creating a vacuum). The greater external pressure (in the main bellows 54) will force any water, located in the collection recess 76, into the pumping bellows 70. When fully expanded, the inlet gap 82 will equalize the pressures within the pumping and main bellows. During the contraction of the main bellows 54, the pumping bellows 70, with its drawn water is forced to also contract. As the pumping bellows 70 contracts and contacts the lower end plate 68, the inlet gap 82 will close and the pressure within the pumping bellows 70 will increase. Eventually, the pressure within the pumping bellows 70 will exceed both the force of the return spring 81 of the one-way valve 80 and the pressure of the outside environment, thus forcing the water from within the pumping bellows 70, past the temporarily open one-way valve 80, and out of the breathing circuit 44.

The compact breathing assembly shown in FIG. 3 operates similar to the system shown in FIG. 2. Again, fresh gas enters into the breathing circuit 44 from the supply circuit 42 through the second stage inlet conduit 48 and the first stage inlet conduit 50. The high pressure fresh gas entering the auxiliary bellows 56 is controlled by the inlet control valve 52. As discussed above, the inlet control valve 52 opens only when the auxiliary bellows 56 is in its collapsed state. The control valve 52 is preferably forced open through direct contact between an actuator arm 84 (used to open the inlet control valve 52) and a contact member 86 formed integrally with the upper end plate 66 of the auxiliary bellows 56.

The third segment **24*c* of the inhalation conduit 24 and the exhalation conduit 28 both extend from the mouthpiece assembly 26 (not shown in FIG. 3) and are preferably affixed to their respective upper and lower side of the center support plate 64**.

In the breathing apparatus shown in FIG. 3, the carbon dioxide absorber 30 is preferably positioned within a recess 88 formed in the upper end plate 66 of the auxiliary bellows 56. An appropriate cover plate 90 covers the recess 88 and secures the carbon dioxide absorber 30 within the recess 88. The recess 88 includes an inlet opening 92 which is connected to a flexible first segment **24*a* (see FIG. 2) which, in turn is connected to the main bellows 54, through an opening 93 formed in the center support plate 64. The flexible conduit 24*a* functions only to provide fluid communication from the main bellows 54 to the carbon dioxide absorber 30, without restricting or otherwise limiting the independent movement of the auxiliary bellows 56. Another opening not shown in FIG. 3 is provided within the recess 88 to function as segment 24*b* of the inhalation conduit 24 (see FIG. 2) to effectively provide fluid (gaseous) communication from the carbon dioxide absorber 30 to the auxiliary bellows 56**.

Figure 1:
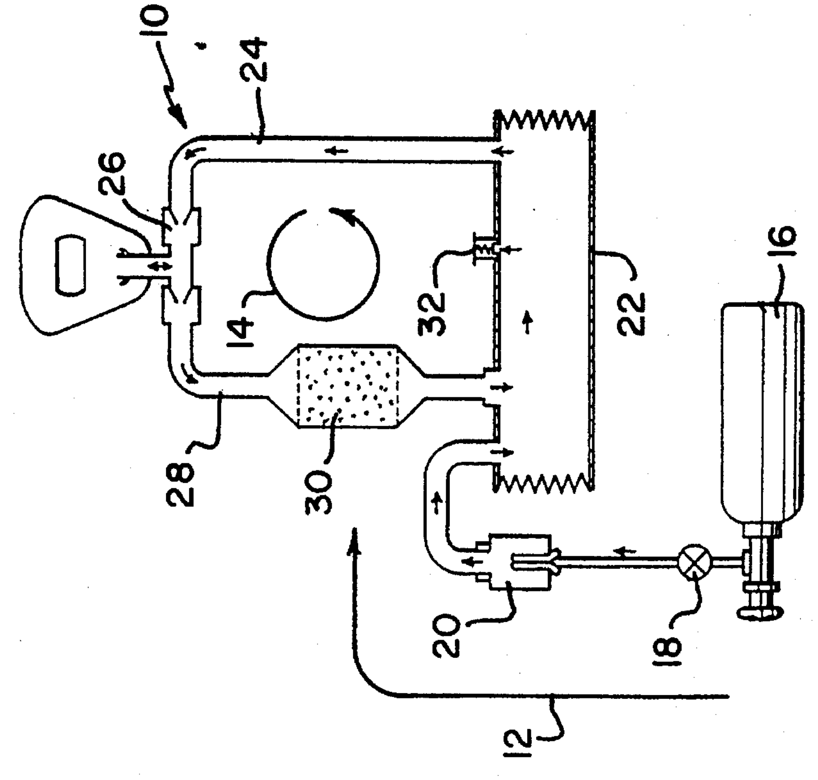
FIG. 1 PRIOR ART
FIG. 1 is a schematic of a prior art semi-closed scuba breathing system.

By repositioning the carbon dioxide absorber 30 from within the exhalation conduit 28 of the prior art breathing system (see FIG. 1) to within the inhalation conduit 24, the water-sensitive absorbing element 30 is protected from exhaled water vapor (and liquid). The purpose of the auxiliary bellows 56 and the high pressure path 60 of fresh gas is to compensate for any restriction to the inhalation gasflow created by the carbon dioxide absorber 30 so that the diver is not unduly burdened as he breathes.

In operation of the auxiliary bellows 56, as the diver inhales, the immediate loss of air from the auxiliary bellows 56 will cause the bellows 56 to collapse. Under normal breathing, even the restricted flow of gas from the carbon dioxide absorber 30 should be sufficient to re-inflate the auxiliary bellows 56 prior to the next breath by the diver. However, should the demand for fresh gas at the mouthpiece assembly 26 be so great as to completely collapse the auxiliary bellows 56 prior to the bellows 56 being re-inflated by the relatively slow restricted gas flow through the carbon dioxide absorber 30, the actuator arm 4 will be triggered through direct contact with the contact member 86, if only for a short moment. The actuator arm 84 will open the inlet control valve 52 which will allow high pressure fresh gas to enter the breathing circuit 44 at the auxiliary bellows 56. The sudden high pressure supply of gas will cause the auxiliary bellows 56 to immediately re-inflate. As the auxiliary bellows 56 expands past a predetermined point, the contact pressure to the actuator arm 84 will cease, thereby automatically re-closing the inlet control valve 52 and the high pressure supply of fresh gas. The breathing demand of the diver is therefore automatically met by the self-regulating auxiliary bellows 56 switching, as necessary, between a slow but efficient fresh gas supply and an immediate "on call" (yet less efficient) supply.

Figure 4:
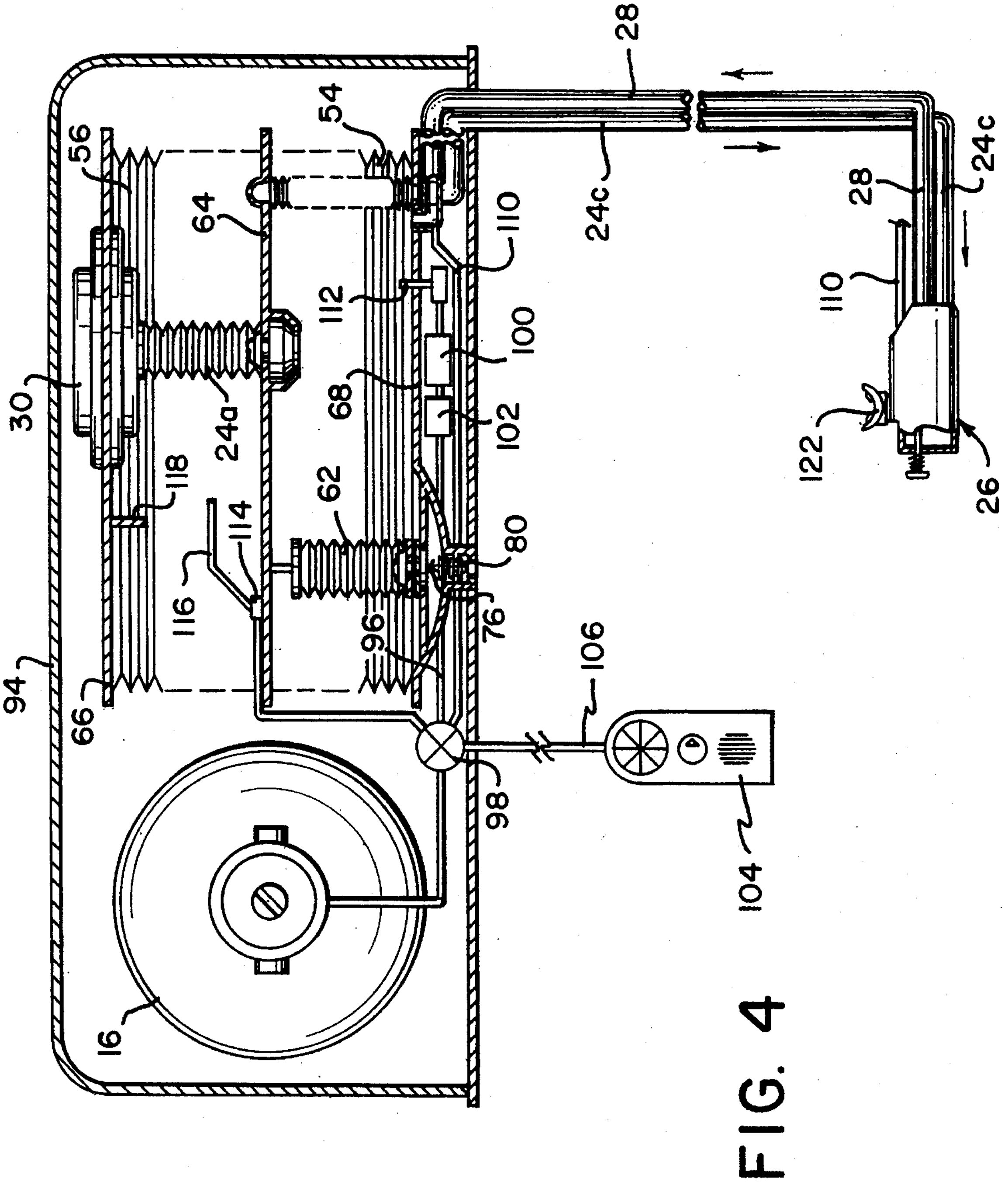
FIG. 4 is a partial sectional top view of the breathing apparatus enclosed in a case in accordance with yet another embodiment the invention.
Figure 5:
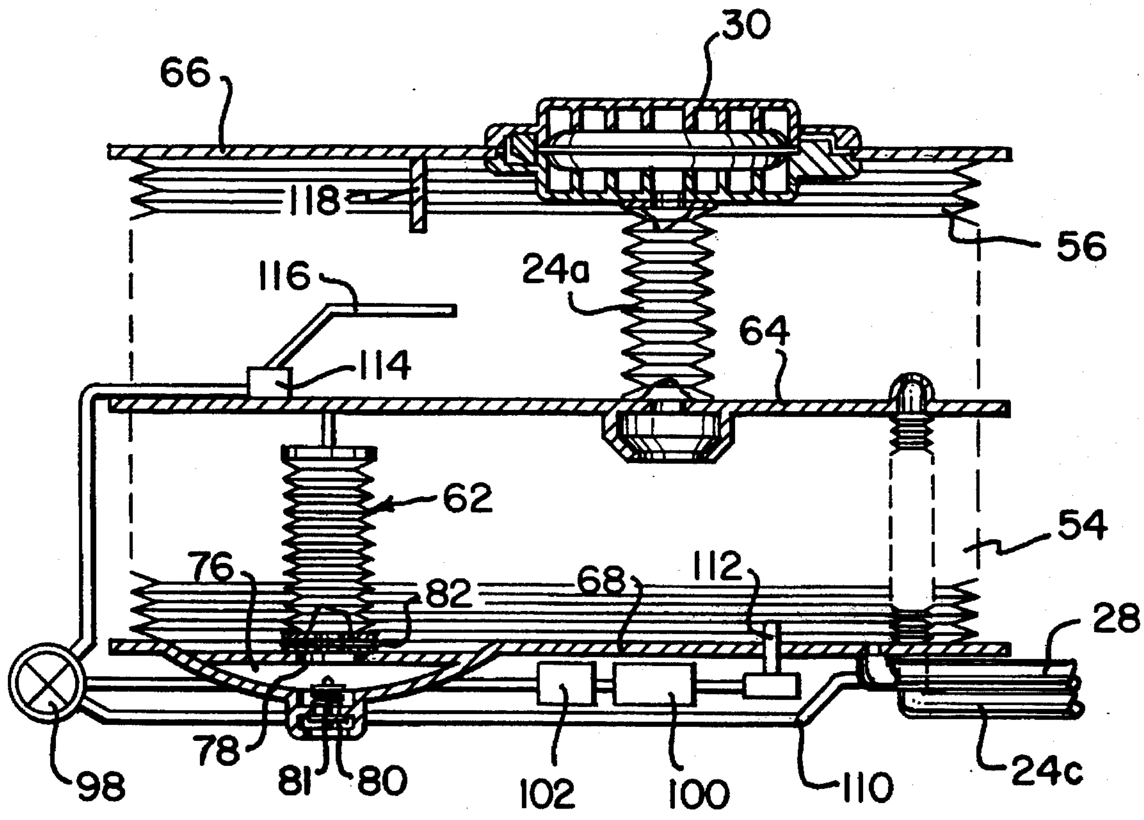
FIG. 5 is an enlarged sectional view of the respiration bellows assembly of FIG. 4.

Referring to FIGS. 4 through 7 another embodiment of the present breathing apparatus is shown enclosed in a casing 94 to be worn on the back of a scuba diver (not shown). The breathing apparatus of FIGS. 4 and 5 is similar to the breathing apparatus described above and shown in FIGS. 2 and 3, yet here the problem being addressed relates to the effect which differences in ambient hydrostatic pressure have on both the main bellows 54 and the auxiliary bellows 56 as the diver maneuvers within the water environment. The construction of the apparatus positions the relatively heavy assembly containing the carbon dioxide absorber 30 to the upper end plate 66 of the auxiliary bellows 56 so that its weight forces the auxiliary bellows 56 to either compress or retract according to the diver's orientation as he swims. The added force supplied by the weight of the assembly containing the carbon dioxide absorber 30 is meant to help simulate a human lung by maintaining the pressure within the main bellows 54 and the auxiliary bellows 56, as further explained below.

As the diver wearing the casing 94 containing the breathing apparatus of FIG. 4 swims with his abdomen facing the ground (or sea floor), the hydrostatic pressure at the depth of the diver's lungs is greater than that at the depth of the main bellows 54 or auxiliary bellows 56. In this position, the weight of assembly containing the carbon dioxide absorber 30 drawn by gravity applies force to the auxiliary bellows 56 and the main bellows 54 urging them to collapse towards the diver's back (and towards the sea floor). The result here is that the internal pressure is maintained similar to that of a human lung. If, on the other hand, the main bellows 54 and the auxiliary bellows 56 are contracted and the diver is in an inverted orientation, i.e., with his back facing the sea floor, the relatively heavy assembly containing the carbon dioxide absorber 30 will be drawn by gravity to help expand the auxiliary bellows 56 and the main bellows 54, against the slightly greater hydrostatic pressure at the depth of the bellows 54, 56.

The rebreathing apparatus of FIGS. 4 and 5 includes, as before, a tank 16 connected to a regulator 98, an auxiliary bellows 56, a main bellows 54, an inhalation conduit 24, an exhalation conduit 28 and a mouthpiece assembly 26. A supply conduit 96 is connected between the regulator 98 and a flow control device 100. A filter 102 is positioned in-line between the regulator 98 and flow control device 100. Also, a diver's hand-held pressure gauge assembly 104 is connected via an appropriate conduit 106 to the regulator 98. The outlet of the flow control device 100 is connected to an inlet conduit 112 directly into the main bellows 54. The flow of gas into the main bellows 54 from the inlet conduit 112 is controlled only by the regulator 98 and the flow control device 100.

A purge supply conduit 110 also extends from the regulator 98 directly to the mouthpiece assembly 26, as described further below.

Similar in operation to the above-described inlet control valve 52, an inlet control valve 114 provided with an actuator arm 116 controls the flow of breathable gas into the auxiliary respiration bellows 56. A contact member 118 is now formed integral with the upper end plate 66 and directed downward into the auxiliary bellows 56.

In operation, should inhalation force the auxiliary respiration bellows 56 to collapse, thereby causing the upper end plate 66 to approach the center support plate 64, the contact member 118 will eventually contact the actuation arm 116 and "open" the control valve 114. Once "opened", the control valve 114 passes fresh breathable gas from the regulator 98 directly into the auxiliary respiration bellows 56 which expands the auxiliary bellows 56 to an acceptable level. The control valve 114 operating with the contact member 118 automatically regulates and retains the inflation of the auxiliary bellows 56.

Figure 6:
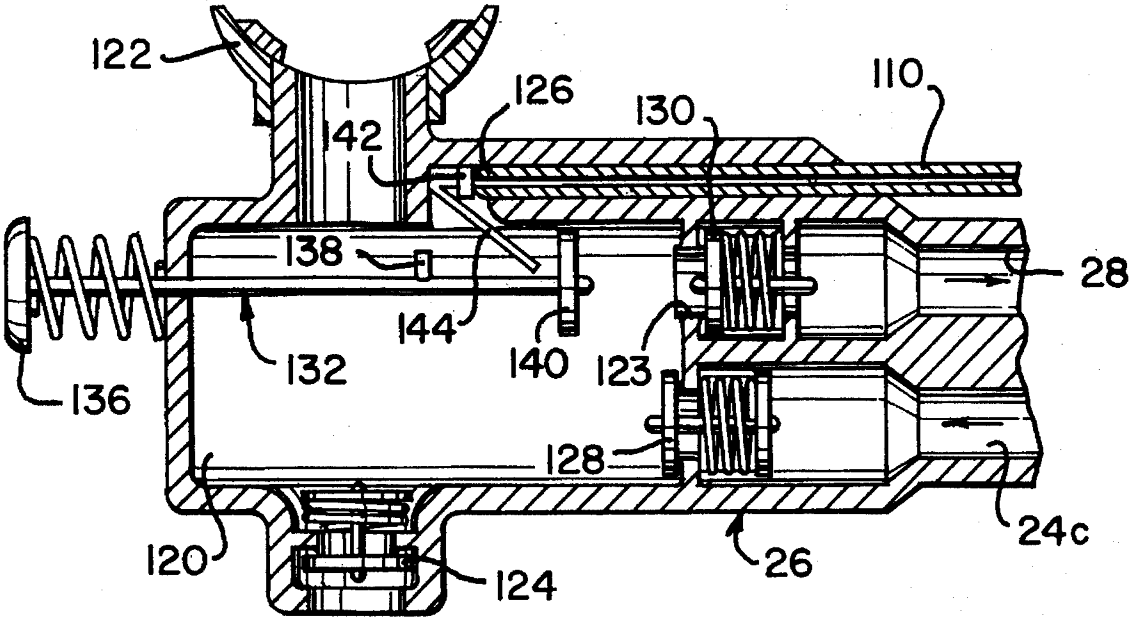
FIG. 6 is an enlarged sectional view of a mouthpiece assembly in accordance with the invention showing a non-purge condition; and, FIG. 7 is an enlarged sectional view of the mouthpiece assembly of FIG. 6 showing a purge condition.
Figure 7:
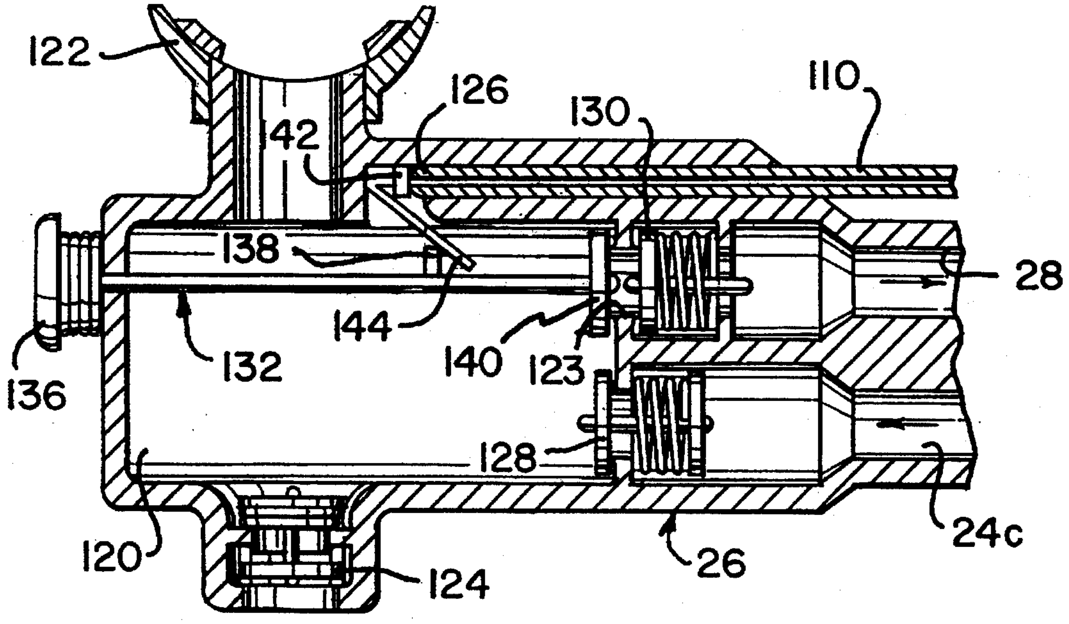

Referring to FIGS. 6 and 7, a mouthpiece assembly 26 in accordance with the invention is shown having three main connecting conduits, an inhalation conduit 24*c*, and exhalation conduit 28 and the purge supply conduit 110 connected to the mouthpiece assembly via a purge supply inlet 126. The mouthpiece assembly 26 includes a respiration chamber 120 to which is connected the inhalation conduit 24*c*, the exhalation conduit 28, a mouthpiece element 122, a purge outlet valve 124 and the purge supply 110. The inhalation conduit 24*c* supplies breathable gas to the diver. As the diver inhales, gas from the inhalation conduit 24*c* passes a spring-loaded, one-way check valve 128, enters the respiration chamber 120 and finally, is inhaled by the diver through the mouthpiece element 122. As the diver exhales, the exhalation gases are directed through an exhale outlet passageway 123, past a spring-loaded, one-way check valve 130 and into the exhalation conduit 28. The two spring-loaded check valves 128, 130 ensure that the diver receives breathable gas only from the inhalation conduit 24*c* and, under normal operation, all exhalation gases leave the mouthpiece assembly 26 through the exhalation conduit 28.

Water vapor or liquid may enter and accumulate in the respiration chamber 120. A purging system is provided to allow the diver to selectively remove the accumulated water from the respiration chamber 120. The purging system includes the purging supply inlet 126, a purge controller 132 and a purge outlet valve 124. The purge controller 132, which is movable by the diver between a purge and a non-purge position is spring-biased to the non-purge position and includes an accessible end 136, a contact member 138 and a sealing element 140. The supply inlet 126 includes a control valve 142 which is normally closed and actuated by an actuator 144. The actuator 144 is positioned to engage with and be actuated by the contact member 138 of the purge controller 132 only when the purge controller 132 is moved (by the diver) to the purge position, shown in FIG. 7.

When the purge controller 132 is moved to the purge position, the actuator 144 "opens" the control valve 142 and the sealing element 140 closes the exhale outlet passageway 123 to direct any supply of purging gas to the purge outlet valve 124 only. As the control valve 142 remains "open", the pressurized gas from the purge supply conduit 110 increases the pressure within the respiration chamber 120. Eventually, the pressure will exceed the force of the return spring of the purge outlet valve 124 and the pressure of the outside environment, at which point any water located at or near the outlet valve 124 will be forced from the respiration chamber 120. The diver should not inhale during initiation of purging, in order to avoid the water to be purged from being forced into the diver's lungs. Once the water has been expelled from the respiration chamber 120, however, the diver may once again breathe normally.

When released, the purge controller 132 automatically returns to the non-purge position, the contact member 138 causes the actuator 144 to close the control valve 142 and the exhale outlet passageway 123 is unsealed.

While the invention has been shown and described with respect to the preferred embodiments relating to underwater rebreathing systems, it will be readily observed and understood by persons of ordinary skill, to which the invention pertains, that the described systems are equally applicable to firefighting rebreathing systems and the like, wherein a user must survive in a hostile, nonbreathable environment, with only self-contained, limited resources. The invention is limited only by the claims.

What is claimed is:

1. A respiration system wherein a first waste gas portion of a user's exhaled breath is removed from the exhaled breath within the system, thereby leaving a second portion of the exhaled breath suitable for rebreathing, said respiration system comprising:

a pressurized breathable gas supply;

a first expansion chamber;

a mouthpiece for providing breathable gas to and receiving exhaled breath from the user, said mouthpiece having an inlet and an outlet, said outlet being connected to said first expansion chamber, said exhaled breath including water;

means for mixing within said first expansion chamber said exhaled breath with breathable gas from said pressurized breathable gas supply to form a gas mixture;

means for separating said water from said exhaled breath;

means for substantially eliminating said separated water from said respiration system, said elimination means including a water pump located within said first expansion chamber, said water pump removing water that has been separated from said exhaled breath from said respiration system;

an inhalation tube connected between said first expansion chamber and said inlet of said mouthpiece, said inhalation tube providing communication of said gas mixture of said first expansion chamber and said mouthpiece; and means for removing at least some of the first waste gas portion from said gas mixture, said removing means being located along said inhalation tube between said first expansion chamber and said mouthpiece.

2. The respiration system according to claim 1 wherein said first expansion chamber operates between a contracted position and an expanded position, said water pump being operationally responsive to said operation of said first expansion chamber.

3. The respiration system according to claim 1 further including a one-way valve for allowing said separated water to be pumped out of said respiration system by said pump.

4. A respiration system wherein a first waste gas portion of a user's exhaled breath is removed from the exhaled breath within the system, thereby leaving a second portion of the exhaled breath suitable for re-breathing, said respiration system comprising:

a pressurized breathable gas supply;

a first expansion chamber;

a mouthpiece for providing breathable gas to and receiving exhaled breath from the user, said mouthpiece having an inlet and an outlet, said outlet being connected to said first expansion chamber, said exhaled breath including water;

means for mixing within said first expansion chamber said exhaled breath with breathable gas from said pressurized breathable gas supply to form a gas mixture;

means for separating said water from said exhaled breath;

means for substantially eliminating said separated water from said respiration system;

an inhalation tube connected between said first expansion chamber and said inlet of said mouthpiece, said inhalation tube providing communication of said gas mixture of said first expansion chamber and said mouthpiece;

means for removing at least some of the first waste gas portion from said gas mixture, said removing means being located along said inhalation tube between said first expansion chamber and said mouthpiece;

means for supplying breathable gas from said breathable-gas supply to said inhalation tube between said removing means and said mouthpiece to compensate for any gas-flow resistance created by said removing means during high demand inhalation by the diver, said means for supplying breathable gas to said inhalation tube comprising a second expansion chamber; and means to compensate for a difference between ambient pressure at a first depth of the diver's lungs and ambient pressure at a second depth of the second expansion chamber when the diver is oriented horizontally.

* * * * *